(12) United States Patent
Chang et al.

(10) Patent No.: US 8,258,317 B2
(45) Date of Patent: Sep. 4, 2012

(54) CATALYST FOR DIRECT CONVERSION OF ESTERS OF LACTIC ACID TO LACTIDE AND THE METHOD FOR PRODUCING LACTIDE USING THE SAME

(75) Inventors: Jong-San Chang, Daejeon (KR); Young-Kyu Hwang, Daejeon (KR); Jung-Ho Lee, Daejeon (KR); Jong-Min Lee, Daejeon (KR); Min-Hee Jung, Gyeonggi-do (KR)

(73) Assignee: Korea Research Institute of Chemical Technology, Daejeon (KR)

( * ) Notice: Subject to any disclaimer, the term of this patent is extended or adjusted under 35 U.S.C. 154(b) by 439 days.

(21) Appl. No.: 12/563,885

(22) Filed: Sep. 21, 2009

(65) Prior Publication Data

US 2010/0298578 A1 Nov. 25, 2010

(30) Foreign Application Priority Data

May 20, 2009 (KR) ........................ 10-2009-0043985

(51) Int. Cl.
*C07D 319/00* (2006.01)
(52) U.S. Cl. ....................................................... 549/274
(58) Field of Classification Search ................... 549/274
See application file for complete search history.

(56) References Cited

U.S. PATENT DOCUMENTS

| 4,424,140 A | 1/1984 | Weinberg et al. |
| 5,247,059 A | 9/1993 | Gruber et al. |
| 5,332,839 A | 7/1994 | Benecke et al. |
| 5,900,491 A * | 5/1999 | Kurashima et al. ............ 549/274 |

FOREIGN PATENT DOCUMENTS

| JP | 1993-286966 | 11/1993 |
| JP | 1994-031175 | 2/1994 |
| JP | 1999-092475 | 4/1999 |
| WO | 92/00292 | 1/1992 |

OTHER PUBLICATIONS

Joglekar et al., "Comparative assessment of downstream processing options for lactic acid", ScienceDirect, Separation and Purification Technology 52, (2006), pp. 1-17.
EP Search Report, dated Apr. 19, 2010, corresponding to EP Application No. 09171147 (filed Sep. 23, 2009), a related application, 5 pp.

* cited by examiner

*Primary Examiner* — Taylor Victor Oh
(74) *Attorney, Agent, or Firm* — Greenlee & Sullivan P.C.

(57) ABSTRACT

The present disclosure discloses a catalyst for directly producing a lactide which is a cyclic ester used as a monomer for polylactides, and a method for directly producing a lactide using the catalyst, the method including the transesterification reaction between two molecules of an ester of lactic acid or a mixture containing the ester of lactic acid with a small amount of lactic acid and oligomer of lactic acid under an inert environment in the presence of a titanium-based catalyst or a catalyst mixture containing the titanium-based catalyst so as to produce lactide while simultaneously removing an alcohol (ROH) generated as a by-product. As compared to a conventional commercialized process, since the method for producing a lactide in accordance with the present disclosure is a novel process capable of directly producing the lactide from the ester of lactic acid, energy consumption is low and the lactide can be produced through a simple process showing a high yield while maintaining optical property (D-form or L-form optical isomer).

18 Claims, 1 Drawing Sheet

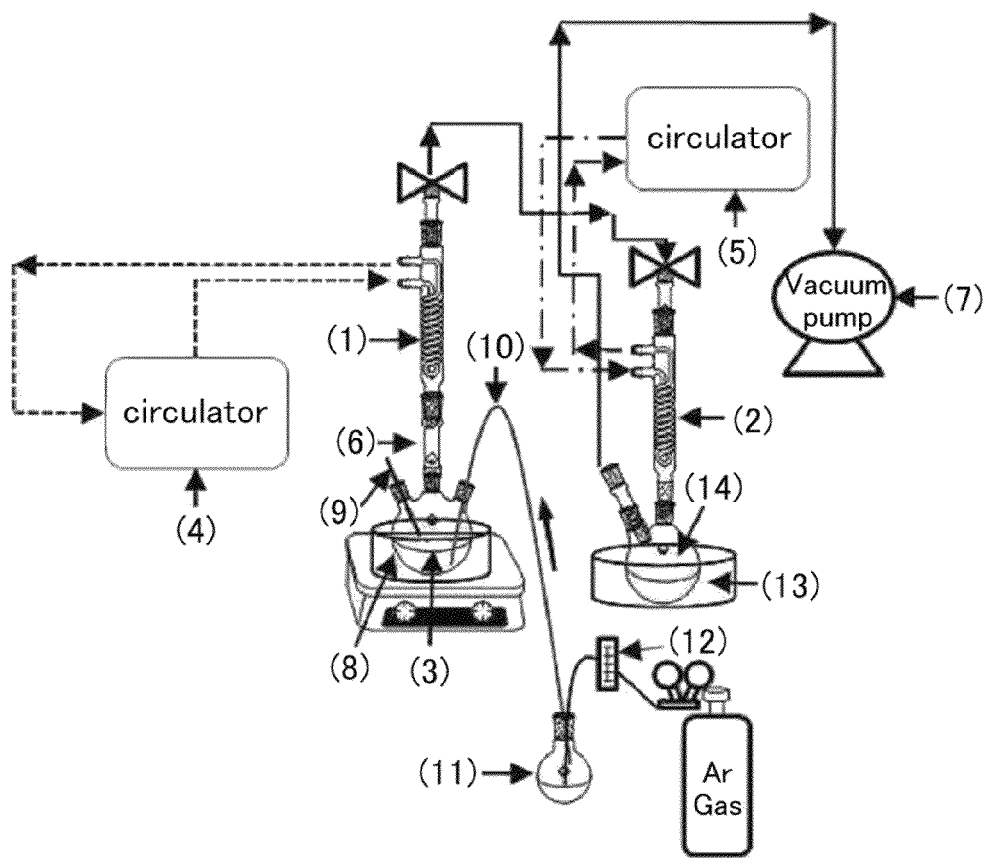

CATALYST FOR DIRECT CONVERSION OF ESTERS OF LACTIC ACID TO LACTIDE AND THE METHOD FOR PRODUCING LACTIDE USING THE SAME

CROSS-REFERENCE TO RELATED APPLICATION

This application claims the benefit of Korean Patent Application 10-2009-0043985 filed on May 20, 2009, which is hereby incorporated by reference in its entirety.

FIELD OF THE INVENTION

The present disclosure relates to a catalyst for direct conversion of an ester of lactic acid to a lactide which is a cyclic ester used as a monomer of polylactide, and also pertains to a method for producing the lactide using the catalyst.

BACKGROUND OF THE INVENTION

Polylactic acid or polylactide (PLA) is a polymer having optical properties and is currently used as a biodegradable medical material such as surgical suture and injection drug capsule. Recently, polylactic acid or polylactide (PLA) can be evaluated as an environmentally-friendly material as well as a biodegradable plastic which can be utilized for producing various kinds of polymer products, such as packaging materials, electric appliances, office supplies, and vehicle upholsteries.

To utilize polylactic acid for the above-mentioned applications, it is required for the polylactic acid to have high optical purity (D-form or L-form optical isomer) and a high molecular weight. For this purpose, lactide used as a monomer for producing the polylactic acid needs to have high optical and chemical purity.

Lactide is a kind of cyclic ester, which is a dimer generated by a dehydration reaction of lactic acid (or by a dealcoholization reaction of an ester compound of lactic acid).

A conventional method for producing lactide has involved the steps of producing a prepolymer having a molecular weight of about 100 to 5,000 by firstly polymerizing lactic acid or ester of lactic acid and then obtaining lactide by depolymerizing the prepolymer in the presence of a catalyst such as a metal oxide-based or tin-based catalyst under a reduced pressure condition with flowing inert gas. For example, U.S. Pat. No. 5,053,522 discloses a technique for producing an optically pure L(−)-lactide or D(+)-lactide by using the above-mentioned method, and U.S. Pat. No. 5,142,023 discloses a method for producing polylactide bioplastics from lactic acid, which includes removing water and a solvent to concentrate the lactic acid since the lactic acid will have to be polymerized to a prepolymer having a low-molecular-weight during the polymerization process due to its particular physical properties when moisture remains. Further, also described in U.S. Pat. No. 5,274,073 is a method for converting crude lactide to a purified lactide or polylactide, including the steps of obtaining a prepolymer by polymerizing lactic acid, then obtaining crude lactide by depolymerizing the prepolymer in the presence of a catalyst, and purifying the crude lactide with a distillation system. Besides, U.S. Pat. No. 5,247,059 discloses a process for producing a sufficiently purified lactide or polylactide from an ester of lactic acid, the process including the steps of producing a polylactide having a low molecular weight by the condensation of the ester of lactic acid using a polymerization catalyst, producing crude lactide by depolymerizing the polylactide having a low molecular weight and purifying the crude lactide. Further, U.S. Pat. No. 5,274,127 discloses a method for producing L-lactide, including the step of dehydrating an aqueous solution of L-lactic acid so that an average degree of polymerization does not exceed 2, and U.S. Pat. No. 6,277,951 describes a method for producing lactide through the steps of producing a polylactide having a low molecular weight from a purified liquid of lactic acid which is obtained by removing water and a solvent therefrom and synthesizing lactide by adding a catalyst to the polylactide having a low molecular weight. Moreover, U.S. Pat. No. 6,326,458 discloses a method of producing purified lactide or polylactide from lactic acid or ester of lactic acid, which includes the step of generating crude polylactide, wherein a catalyst is added to facilitate the generation of the lactide when the ester of lactic acid is used. However, the aforementioned production methods have drawbacks in that the depolymerization speed is slow, deterioration in optical purity occurs due to a high-temperature treatment, and there is difficulty in selecting the form and material of a reactor. Further, the lactides generated by the above-mentioned methods need to be subjected to an additional purifying process by recrystallization or distillation, which results in problems that the processes are complicated and excessive energy is required.

Meanwhile, U.S. Pat. No. 5,319,107 pertains to a method for producing cyclic ester such as lactide or glycolide from hydroxy carboxylic acid or its derivatives, and U.S. Pat. No. 5,420,304 describes a method of generating cyclic ester such as lactide by recovering lactic acid from a dilute lactic acid-containing solution by a solvent extraction method and converting the lactic acid to cyclic ester such as lactide while controlling a production proportion of oligomers having a high molecular weight during the dehydration process. Furthermore, disclosed in Japanese Patent Laid-open Publication No. 1993-286966 is a method for producing lactide having a low hygroscopic property from butyl ester of lactic acid. Besides, Japanese Patent Laid-open Publication No. 1999-209370 discloses a method for producing polylactide or lactide along with monobutyl tin compound by heating and then dealcoholizing an ester of lactic acid in the presence of monobutyl tin compound catalyst. Moreover, Japanese Patent Laid-open Publication No. 2001-181273 discloses a method for producing a polymer of α-hydroxy organic acid having a high molecular weight, including the steps of producing a higher alcohol ester of α-hydroxy organic acid oligomer by the dealcoholization and condensation of an α-hydroxy organic acid ester and a higher alcohol and removing glycolides by heating the higher alcohol ester thus obtained under a reduced pressure.

Further, U.S. Pat. No. 6,875,839 discloses a method for producing polylactide, including the steps of obtaining lactic acid from a starchy agricultural product by fermentation, purifying the lactic acid by ultrafiltration, nanofiltration, and/or electrodialysis, providing a prepolymer and performing a depolymerization process to obtain a dilactide. Moreover, U.S. Pat. No. 6,569,989 discloses a method for producing lactide, including the steps of synthesizing ester of lactic acid from ammonium lactate (ammonium salt of lactic acid) obtained by fermentation, performing a condensation-polymerization of the ester of lactic acid in the presence of a catalyst and depolymerizing the polylactide. In addition, disclosed in Japanese Patent Laid-open Publication No. 1995-304763 is another method for producing lactide, including the steps of producing oligomers of lactic acid from a mixture of lactic acid and ester of lactic acid, and heating and polymerizing the oligomers of lactic acid. Though the above-mentioned various methods have advantages in common in that a process load in the depolymerization step can be reduced by producing, in the prepolymerization step, the oligomers having a high content of lactyl lactate which is a linear dimer of the lactic acid or ester of lactic acid, these methods are not deemed to improve the conventional methods in view of the applied process steps and necessity for a depolymerization process.

Further, U.S. Pat. No. 5,332,839 pertains to a method for directly converting lactide from a lactic acid-containing solution, including direct condensation of lactic acid or oligomer of lactic acid (having a degree of polymerization equal to or less than about 4) in the presence of a fixed-bed catalyst, and Japanese Patent Laid-open Publication No. 1999-092475 relates to a method involving the 2 molecule condensation-cyclization of lactic acid and/or ammonium salt of lactic acid and recovering lactide from a distillation tower. However, these methods have a defect in that deactivation problem of catalysts is serious, making it difficult to carry out a continuous process. Further, as for the technique of recovering only the lactide from the distillation tower, a production yield of lactide is low, and it has been difficult to obtain high-purity lactide from non-reacted lactic acid or oligomer of lactic acid (linear dimer or trimer of lactic acid, or the like).

Meanwhile, though high-purity lactic acid is required as a raw material to obtain a lactide monomer having purity for polymerization, it is difficult to purify the lactic acid because the lactic acid readily forms oligomer in a concentration process. Accordingly, to obtain a high-purity lactic acid from fermented liquid of lactic acid, it is general to pre-treat the fermented liquid, convert it to an ester compound of lactic acid, and purify the ester compound of lactic acid followed by hydrolysis thereof, to thereby obtain high-purity lactic acid (Separation and Purification Technology 52, (2006), 1-17). Accordingly, compared to obtaining lactide by pre-polymerizing the high-purity lactic acid obtained by the above-described method and again depolymerizing the obtained prepolymer, the direct conversion of the ester compound of lactic acid to the lactide is deemed to be a more efficient way to simplify the process and reduce energy consumption greatly.

As a known technology to directly convert ester of lactic acid to lactide, disclosed in Japanese Patent Laid-open Publication Nos. 1999-036366 and 1993-286966 is a method for the condensation of ester of lactic acid containing an alkyl group having 1 to 8 carbon atoms with heating under a reduced pressure condition using a catalyst such as an organic tin compound such as mono-butyl tin oxide, dibutyl tin oxide, dibutyl tin lactate, stannous octonate or the like, zinc chloride ($ZnCl_2$), tin chloride ($SnCl_2$), calcium chloride ($CaCl_2$), phosphoric acid ($H_3PO_4$), p-toluenesulfonic acid, or the like. Furthermore, Japanese Patent Laid-open Publication No. 1994-031175 discloses a method for producing lactide by performing a 2-molecule condensation-cyclization of ester of lactic acid containing a lower alkyl group having 1 to 6 carbon atoms in the presence of dibutyl tin chloride catalyst or a catalyst made of a combination of dibutyl dichloro tin, and phosphorus pentoxide or phosphorus trioxide.

However, the above-stated method using the organic tin catalyst is disadvantageous in that a production proportion of Meso-form optical isomer is high while a yield of lactide is low.

In view of the foregoing, the present inventors have conducted many researches to develop a method for directly converting lactide from ester of lactic acid with a high yield of lactide while maintaining optical property (D-form or L-form optical isomer), and finally reached the present invention which relates to a method for producing lactide directly from ester of lactic acid using a titanium-based catalyst, which shows a high yield while maintaining optical property (D-form or L-form optical isomer).

BRIEF SUMMARY OF THE INVENTION

The present disclosure provides a method for directly producing lactide, which is used as a monomer of polylactide, from ester of lactic acid itself or a mixture containing ester of lactic acid itself with a small amount of lactic acid and/or an oligomer of lactic acid.

The present disclosure also provides a catalyst used in the above producing method, for the direct conversion of the ester of lactic acid itself or a mixture containing the ester of lactic acid with a small amount of lactic acid and/or an oligomer of lactic acid to lactide.

In accordance with one aspect of the present disclosure, there is provided a method for directly producing a lactide, which includes performing a transesterification reaction between two molecules of an ester of lactic acid having the following Chemical Formula (1) as a starting material under an inert environment in the presence of a titanium-based catalyst or a catalyst mixture containing the titanium-based catalyst so as to produce a lactide of the following Chemical Formula (2) while simultaneously removing alcohol of the formula ROH generated as a by-product, according to the following
Reaction Scheme 1:

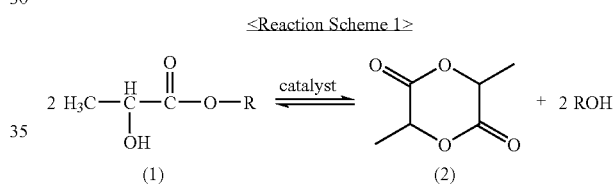

wherein R is a lower alkyl group having from 1 to 4 carbon atoms.

In accordance with another aspect of the present disclosure, there is provided a titanium-based catalyst, which is used for producing a lactide of the above Chemical Formula (2) directly from an ester of lactic acid as a starting material of the above Chemical Formula (1) according to the above Reaction Scheme 1, or a catalyst mixture including the titanium-based catalyst.

Since the method for producing a lactide in accordance with the present disclosure is a novel method to enable the direct production of the lactide from an ester of lactic acid itself or a mixture containing a small amount of lactic acid and an oligomer of lactic acid, energy consumption is reduced as compared to a conventional commercialized process. Further, as a new method capable of producing the lactide with a high yield through a simple process while maintaining optical property (D-form or L-form optical isomer), the method according to the present invention has a high industrial applicability.

BRIEF DESCRIPTION OF THE DRAWINGS

The disclosure may best be understood by reference to the following description taken in conjunction with the following figures:

FIG. 1 is a schematic view of a reaction system that produces a lactide from a lactic acid in accordance with the present disclosure.

DETAILED DESCRIPTION OF THE INVENTION

The present disclosure provides a method for directly producing lactide, which includes performing a transesterification reaction between two molecules of an ester of lactic acid according to Chemical Formula (1) as a starting material under an inert environment, in the presence of a titanium-based catalyst or a catalyst mixture containing the titanium-based catalyst to thereby produce lactide of Chemical Formula (2) while simultaneously removing alcohol of the formula ROH generated as a by-product, as indicated by the following Reaction Scheme 1:

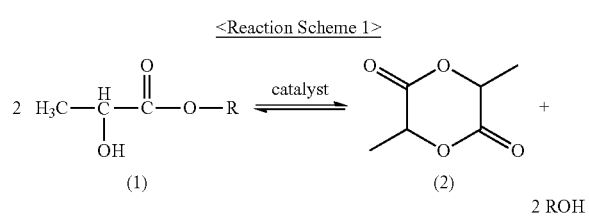

The production method in accordance with the present disclosure desirably includes removing the generated alcohol ROH to obtain the lactide with a high yield in a short time. In this regard, when the alcohol ROH generated as the by-product in the above production method remains together with the lactide of Chemical Formula (2), there may easily occur a reverse reaction to the ester of lactic acid of Chemical Formula (1) as the starting material, or a conversion reaction to oligomer (when n is equal to or larger than 2) containing lactyl lactate of Chemical Formula (3) which is a linear dimer (in case of n=1). Thus, it is important to remove the alcohol generated by the transesterification reaction of Chemical Formula (1) from the reaction system as quickly as possible. Accordingly, to facilitate the removal of the alcohol, the substituent R in the ester of lactic acid of Chemical Formula (1) and the generated alcohol may be desirable to be a lower alkyl group having 1 to 4 carbon atoms. For example, an alkyl lactate (or an ester of lactic acid) having methyl, ethyl, n-propyl, isopropyl, t-butyl, isobutyl, n-butyl, or the like may be used. Meanwhile, although the lactide of Chemical Formula (2) can also be produced by a production method through a route of the following Reaction Scheme 2, oligomer having a high degree of polymerization as well as lactide can be generated from lactyl lactate of Chemical Formula (3) in a catalyst/reaction system where such a reaction is carried out, thereby resulting in that selectivity to the lactide decreases and the reaction time increases.

Further, in the production method of lactide according to the present disclosure, a mixture containing the ester of lactic acid with an amount of about 20% or less by weight of lactic acid or oligomer of lactic acid or a mixture thereof in addition to the ester of lactic acid may be also used as the starting material.

In a fermentation process of lactic acid, salt of lactic acid such as lactic acid ammonium salt, lactic acid calcium salt, lactic acid, or a mixture of lactic acid and lactic acid salt may be generated depending on a fermentation strain and a pH condition. In a process of esterifying these fermented compounds or concentrating the lactic acid, oligomer of lactic acid may be produced in reaction materials, so that the mixture containing the lactic acid and the oligomer of lactic acid as well as the ester of lactic acid may be used as a reaction material. If the content of the lactic acid and the oligomer of lactic acid besides the ester of lactic acid exceeds 20% by weight, selectivity in the transesterification reaction from the ester of lactic acid to the lactide may be deteriorated. However, if their content is not greater than 20% by weight, the selectivity to the lactide production is not greatly affected by their presence. In this case, it is desirable that the lactic acid and the oligomer of lactic acid do not contain moisture in consideration of the characteristics of the catalyst and the reaction system.

Further, in the lactide production method according to the present disclosure, as the titanium-based catalyst, titanium tetraalkoxides $(R'O)_4Ti$, titanium halides $TiX_4$ or $TiX_3$ ($X=F$, Cl or Br), alkoxy titanium halides $(R'O)_{4-x}TiX_x$ ($X=F$, Cl, or Br, x=1 to 3), titanium acetylacetonates $Ti(acetylacetonate)_2$, titanium alkoxide acetylacetonates $Ti(acetylacetonate)(OR')_2$ or the like may be used. Here, a substituent R' of these catalysts may be desirable to be a lower alkyl group having 1 to 4 carbon atoms, and it may be more desirable that R' is an alkyl substituent having the same number of carbon atoms as that of the substituent R of the above-described Chemical Formula (2).

As indicated by the following Reaction Schemes 3 or 4, an actual catalyst activation state of the titanium-based catalyst in accordance with the present disclosure is deemed to be achieved as the alkoxy group or halide group participates in the reaction while being exchanged with a group of the ester of lactic acid serving as a reaction material. Further, as indicated by the following Reaction Scheme 5, alcohol separated from the catalyst can be converted to an ester of lactic acid by substituting its alcohol group through the reaction of the alcohol with the ester of lactic acid or the lactide as a product.

When the alkyl group R of the ester of lactic acid and the alkyl group R' of the titanium-based catalyst are different from each other, they may exist as two different kinds of esters of lactic acid and oligomers of lactic acid. As a consequence, when they remain unreacted, separation/recovery process may become complicated. Thus, in consideration of a post-process, it is desirable that the R and R' are the same alkyl group having the same number of carbon atoms.

Furthermore, in the above-stated aspect, a titanium-based compound obtained by substituting the alkoxy group or the

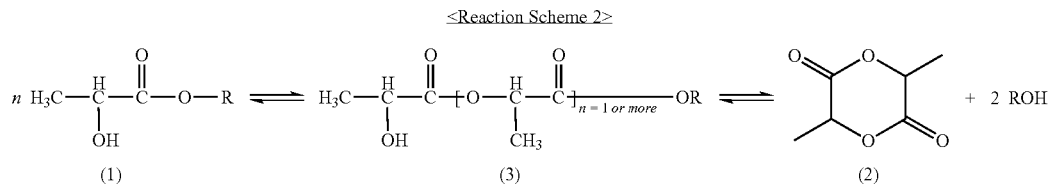

halides group with at least one Q-oxy group of an ester of lactic acid may be also used as well as the above-described titanium-based catalyst.

Moreover, the catalyst mixture containing the titanium-based catalyst in accordance with the present disclosure may contain about 0.1 to 30% by weight of at least one member selected from the group consisting of aluminum (Al), silicon (Si), tin (Sn), zirconium (Zr), niobium (Nb), molybdenum (Mo), tungsten (W), yttrium (Y), gallium (Ga) and a mixture of at least two of them, which are capable of forming an alkoxide, in addition to the titanium-based catalyst. If the content of the metal component capable of forming alkoxide is less than 0.1% by weight, the metal component capable of forming alkoxide which is additionally contained in the titanium-based catalyst may not be sufficiently provided. If the content exceeds 30% by weight, selectivity to lactide may be deteriorated.

Furthermore, besides the titanium-based catalyst, a heterogeneous esterification catalyst in which the titanium-based catalyst is supported on the surface of surface-modified silica or titania may be additionally used to facilitate a recovery of the catalyst after the reaction.

<Reaction Scheme 3>

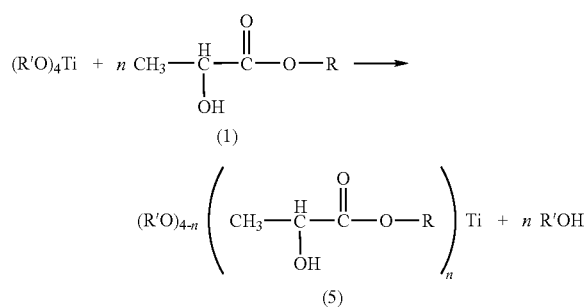

<Reaction Scheme 4>

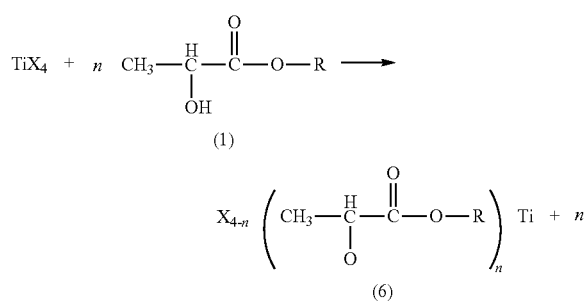

<Reaction Scheme 5>

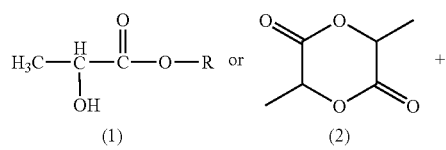

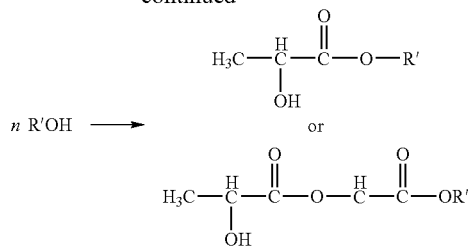

(In the above Reaction Schemes 3, 4 and 5, each of R and R' is a lower alkyl group having 1 to 4 carbon atoms; X is a halogen atom; and n is an integer ranging from 1 to 4.)

Further, an amount of the titanium-based catalyst or the catalyst mixture containing the titanium-based catalyst used in the reaction may be desirably in the range of about 0.01 to 10 mole % with respect to the ester of lactic acid of Chemical Formula (1), and more desirably, in the range of 0.05 to 3 mole %. If the amount of the catalyst is less than 0.01 mole %, a catalyst effect may not be exerted sufficiently and the reaction time becomes prolonged. Meanwhile, if the amount of the catalyst exceeds 10 mole %, the catalyst effect may not be greatly improved as compared to the amount of the catalyst used.

Further, the lactide production method according to the present disclosure provides lactide as an optically pure single isomer form (either L-form or D-form), which can be accomplished by using the ester of lactic acid of Chemical Formula (1) as the reaction material which is a single isomer form of either L-form or D-form. Therefore, the lactide produced by the present method can maintain optical property of the ester of lactic acid as the reaction material.

Furthermore, in the lactide production method according to the present disclosure, a reaction temperature may be maintained constant or may be gradually raised starting the reaction from a low temperature. Specifically, the reaction temperature may be desirably in the range of about 30 to 250° C. and, more desirably, in the range of about 70 to 180° C. If the reaction temperature is below 30° C., the reaction rate may be low, whereas if the reaction temperature exceeds 250° C., the reaction may not successfully proceed due to excessive boiling of the ester of lactic acid serving as the reaction material.

In addition, in the lactide production method according to the present disclosure, the above-described reaction can be carried out under a constant pressure condition to efficiently remove alcohol as the by-product from the reaction system, and a pressure can be gradually reduced as the reaction time passes. For example, the constant pressure condition may be in the range of about 1 to 750 mmHg, and the reduced pressure condition may be desirably performed in the range of about 1 to 750 mmHg, more desirably, in the range of about 20 to 700 mmHg. If the pressure is less than 1 mmHg, energy consumption for maintaining a vacuum may be large. Meanwhile, if the pressure is above 750 mmHg, the separation of the alcohol from the reaction system may not be readily performed, resulting in that a reverse reaction to a linear dimer of Chemical Formula (3) may occur due to a reaction of the alcohol with the lactide as shown in the Reaction Scheme 2 and thus the selectivity to lactide is greatly deteriorated.

Moreover, in the lactide production method according to the present disclosure, the ester of lactic acid of the Chemical Formula (1) as the starting material can be intermittently supplied to the reaction system as the reaction time passes. As the alcohol generated as the by-product makes a reverse reaction with the lactide which is the reaction product, the ester of lactic acid as the starting material also reacts with the lactide, thus resulting in the generation of the oligomer of ester of lactic acid. Accordingly, in order to prevent deterioration of selectivity to the lactide and reduce a reaction time, it may be desirable to feed the ester of lactic acid intermittently.

In this case, a feeding rate of the ester of lactic acid as the starting material may range from 10 to 300 molar ratio, and preferably from 30 to 200 molar ratio of the ester of lactic acid per one mole of the catalyst per hour. If the feeding rate is as low as less than 10 molar ratio of the ester of lactic acid per one mole of the catalyst per hour, a reaction rate may become slow when the ester of lactic acid is fed. Meanwhile, if the feeding rate is as fast as more than 300 molar ratio, an effect of the reaction with the ester of lactic acid may be deteriorated.

Further, the lactide production method in accordance with the present disclosure can be carried out using a solvent or without using a solvent. In case of using a solvent, a solvent having a boiling point higher than that of the ester of lactic acid may be desirably used in order to allow the reaction to progress smoothly by avoiding that the condensation reaction is inhibited due to the produced lactide. The solvent may be selected from the group consisting of tri ethyleneglycol dimethyl ether, tetraethyleneglycol dimethyl ether, γ-butyrolactone and dimethyl ether.

Furthermore, the present disclosure provides a titanium-based catalyst, which is used for producing a lactide directly from an ester of lactic acid as a starting material containing an alkyl group having 1 to 4 carbon atoms represented by Chemical Formula (1) in the above-mentioned Reaction Scheme 1.

Desirably, the titanium-based catalyst may be titanium tetraalkoxides $(R'O)_4Ti$, titanium halides $TiX_4$ or $TiX_3$ (X=F, Cl or Br), alkoxy titanium halides $(R'O)_{4-x}TiX_x$ (X=F, Cl, or Br, x=1 to 3), titanium acetylacetonates $Ti(acetylacetonate)_2$, or titanium alkoxide acetylacetonates Ti (acetylacetonate) $(OR')_2$. Here, a substituent R' of these catalysts may be desirable to be a lower alkyl group having 1 to 4 carbon atoms, and it may be more desirable that R' is a substituent having the same number of carbon atoms as that of the above-described alkyl group substituted in the ester of lactic acid. This titanium-based catalyst is capable of exhibiting high activity and selectivity regardless of the kind of the L-form or D-form optical isomer of the ester of lactic acid in the starting material for producing the lactide.

Further, the titanium-based catalyst in accordance with the present disclosure may desirably further contain about 0.1 to 30% by weight of at least two members selected from the group consisting of aluminum (Al), silicon (Si), tin (Sn), zirconium (Zr), niobium (Nb), molybdenum (Mo), tungsten (W), yttrium (Y) and gallium (Ga), which are capable of forming an alkoxide, in addition to the titanium-based catalyst.

Furthermore, as the titanium-based catalyst in accordance with the present disclosure, a heterogeneous esterification catalyst in which the above-described titanium-based catalyst is supported on the surface of surface-modified silica or titania may be included as well as the titanium-based catalyst. For example, a heterogeneous catalyst can be produced by controlling an OH concentration on the surface of a support having a large surface area, such as silica, mesoporous materials, organic/inorganic mesoporous materials, organic polymers, or the like using a silane coupling agent compound as an organic functional group and then supporting the above-mentioned titanium-based organic metal or metal compound thereon, and the heterogeneous catalyst as obtained may be used for producing the lactide monomer in order to facilitate a recovery of the catalyst after the reaction.

The process for producing the lactide, which is used as the monomer of polylactide, from the ester of lactide in accordance with the present disclosure can be performed by the reaction system illustrated in FIG. 1. In the reaction system, reference numerals 1 and 2 denote condensers, and reference numerals 4 and 5 denote coolant circulators. A connector 6 is connected between a capacitor 1 and a reactor 3, and the outside thereof is wrapped with a heating tape. A pressure is maintained by using an automatic pressure-controlling vacuum pump 7. The temperature of the reactor 3 is maintained by using a silicone oil bath 8, and the temperature of the reaction material is checked by a thermocouple 9. The ester of lactic acid itself or a mixture containing the ester of lactic acid as the starting material is placed in a one-neck round-bottom flask 11. The ester of lactic acid itself or the mixture containing the ester of lactic acid as the starting material is introduced into the inside of the reactor by using a cannula 10. A flow rate of argon gas is controlled by means of a fine control valve 12, and ethanol generated along with the lactide is condensed and collected in a 2-neck round-bottom flask 14 submerged in an ice bath 13.

Hereinafter, the present disclosure will be described in more detail with reference to the following examples. However, it should be noted that the scope of the present invention is not limited thereto.

EXAMPLES

Example 1

Synthesis of L-Lactide 1

In a reaction apparatus depicted in FIG. 1, a temperature of a recycling coolant in a condenser 1 was adjusted to 20° C., and a temperature of a recycling coolant in a condenser 2 was adjusted to −10° C.

A three-neck round bottomed flask from which moisture was sufficiently removed was purged with a highly pure Ar gas, and 0.17 mol of Triethyleneglycol dimethyl ether (TEGDME, purchased from Aldrich, dried over molecular sieves) and $2.5 \times 10^{-3}$ mol of titanium ethoxide [$Ti(OEt)_4$, purchased from Acros] were added into the flask, and the flask was then equipped as depicted in FIG. 1. Then, 0.34 mol of L-ethyl lactate (chemical purity of 98%, optical purity of 98.1%) which is the ester of lactic acid as the starting material was introduced in a vial from which moisture and air were removed and the vial was connected to the reactor using a cannula. A pressure of the reaction system was maintained at 50 mmHg by operating a vacuum pump while flowing Ar gas at 20 mL/min in the reaction system. The reactor at the above condition was placed into an oil bath maintained at 120° C. and then stirred to confirm to reach thermal equilibrium, and L-ethyl lactate was intermittently injected. After the injection of 0.17 mol of L-ethyl lactate was completed for 1.5 hours, the reaction was performed for total 6 hours so as to produce lactide.

Example 2

Synthesis of L-Lactide 2

The reaction was performed in the same manner as in Example 1 except that a temperature of a recycling coolant in a condenser 1 was adjusted to 30° C., and a reaction pressure was adjusted to 210 mmHg. After the reaction was performed for 4 hours at 210 mmHg, the reaction pressure was lowered to 50 mmHg and the reaction was continuously performed for additional 2 hours so as to produce lactide.

Example 3

Synthesis of L-Lactide 3

The reaction was performed in the same manner as in Example 1 to produce lactide, except that a mixture containing L-ethyl lactate with L-lactic acid and an oligomer of lactic acid which were 10% by weight with respect to L-ethyl lactate.

Example 4

Synthesis of L-Lactide 4

The reaction was performed in the same manner as in Example 1 to produce lactide, except that $2.7 \times 10^{-3}$ mol of titanium tetrachloride (TiCl$_4$, Aldrich) instead of titanium ethoxide was used as a catalyst for producing lactide and that L-ethyl lactate of about $4.2 \times 10^{-2}$ mol together with TEGDME and TiCl$_4$ were simultaneously introduced into the reactor in FIG. 1 so that a chloride anion was substituted by ethyl lactate.

Comparative Example 1

Synthesis of L-Lactide 5

The reaction was performed in the same manner as in Example 1 to produce lactide, except that all of L-Ethyl lactate, TEGDME and TiCl$_4$ were simultaneously introduced into the reactor in FIG. 1 at the beginning of the reaction.

In the case of the above reaction, the initial reaction temperature did not exceed 75° C. due to boiling of L-ethyl lactate and alcohol generated from the reaction, and then the reaction temperature was gradually raised as the reaction proceeded.

Comparative Example 2

Synthesis of L-Lactide 6

Instead of titanium ethoxide, tin compound, which is a known catalyst, was used as a catalyst for producing lactide. The reaction was performed in the same manner as in Example 1 to produce lactide, except that the reaction was performed using $2.7 \times 10^{-3}$ mol of tin octanoate [Sn(Oct)$_2$, Aldrich].

Test Example 1

Analyses of Conversion Ratio and Selectivity According to Injection Methods of L-Ethyl Lactate To analyze conversion ratio and selectivity according to injection methods of L-ethyl lactate, the reaction products were analyzed using FID-GS Gas Chromatograph (DS 6200, DONAM INSTRUMENTS, INC.) with DB-2000 (30 m×0.53 μm×1 μm, Agilent Tech.) column and Cyclosil B column (Agilent Tech) for separating optical isomers, and the results are shown in Table 1.

TABLE 1

| Examples | Conversion ratio L-ethyl lactate | Selectivity (%) L-lactide | Meso-lactide | D-lactide |
|---|---|---|---|---|
| Example 1 | 98.0 | 88.7 | 1.93 | 0.15 |
| Comparative Example 1 | 87.2 | 67.1 | 1.87 | 0.17 |

Referring to Table 1, the conversion ratio of L-ethyl lactate was 98.0% and the selectivity to each of L-lactide, Meso-lactide and D-lactide was 88.7%, 1.93% and 0.15%, respectively, in case of Example 1 in which L-ethyl lactate was intermittently injected. Meanwhile, in case of Comparative Example 1 in which L-ethyl lactate was simultaneously injected at the beginning of the reaction, the conversion ratio of L-ethyl lactate was 84.5% and the selectivity to L-lactide was 63.0% after the 6-hour reaction, and the conversion ratio of L-ethyl lactate was 87.2% and the selectivity to L-lactide was 67.1% after the 8-hour reaction. The selectivity to Meso-lactide was 1.87% and the selectivity to D-lactide was 0.17%.

Accordingly, it can be found that conversion ratio of L-ethyl lactate and selectivity to L-lactide increase when L-ethyl lactate is intermittently injected.

Test Example 2

Analyses of Conversion Ratio and Selectivity under Conditions of Constant Pressure and Reduced Pressure To analyze conversion ratio and selectivity under conditions of a constant pressure and a reduced pressure, the reaction products were analyzed using gas chromatography, and the results are shown in Table 2.

TABLE 2

| Examples | Conversion ratio L-ethyl lactate | Selectivity (%) L-lactide | Meso-lactide | D-lactide |
|---|---|---|---|---|
| Example 1 | 98.0 | 88.7 | 1.93 | 0.15 |
| Example 2 | 97.6 | 77.3 | 1.98 | 0.1 or less |

Referring to Table 2, the conversion ratio of L-ethyl lactate was 98.0% and the selectivity to each of L-lactide, Meso-lactide and D-lactide was 88.7%, 1.93% and 0.15%, respectively, in case of Example 1 in which the reaction was performed under the constant pressure. Meanwhile, in case of Example 2 in which the reaction was performed under the reduced pressure, the conversion ratio of L-ethyl lactate was 97.6% and the selectivity to each of L-lactide, Meso-lactide and D-lactide was 77.3%, 1.98% and 0.1% or less, respectively after the 6-hour reaction.

Accordingly, it can be found that the conversion ratio of Example 2 is similar to that of Example, but the selectivity to L-lactide was lowered in Example 2.

Test Example 3

Analyses of Conversion Ratio and Selectivity in Each Case of Using an Ester of Lactic Acid And a Mixture Containing an Ester of Lactic Acid To analyze conversion ratio and selectivity in each case of using an ester of lactic acid and a mixture containing the ester of lactic acid, the reaction products were analyzed using gas chromatography, and the results are shown in Table 3.

TABLE 3

| Examples | Conversion ratio L-ethyl lactate | Selectivity (%) | | |
|---|---|---|---|---|
| | | L-lactide | Meso-lactide | D-lactide |
| Example 1 | 98.0 | 88.7 | 1.93 | 0.15 |
| Example 3 | 96.2 | 84.5 | 1.96 | 0.1 or less |

Referring to Table 3, the conversion ratio of L-ethyl lactate was 98.0% and the selectivity to each of L-lactide, Meso-lactide and D-lactide was 88.7%, 1.93% and 0.15%, respectively, in case of Example 1 in which the ester of lactic acid was used as a starting material. Meanwhile, in case of Example 3 in which the mixture containing 10% by weight of both L-lactic acid and an oligomer of lactic acid with respect to L-ethyl lactate was used, the conversion ratio of L-ethyl lactate was 96.2% and the selectivity to each of L-lactide, Meso-lactide and D-lactide was 84.5%, 1.96% and 0.1% or less, respectively.

Accordingly, it can be found that the selectivity to L-lactide is not affected even when a small amount of L-lactic acid and an oligomer of lactic acid as the starting material is contained.

Test Example 4

Analyses of Conversion Ratio and Selectivity According to Titanium-Based Catalysts for Producing Lactide To analyze conversion ratio and selectivity according to titanium-based catalysts for producing lactide, the reaction products were analyzed using gas chromatography, and the results are shown in Table 4.

TABLE 4

| Examples | Conversion ratio L-ethyl lactate | Selectivity (%) | | |
|---|---|---|---|---|
| | | L-lactide | Meso-lactide | D-lactide |
| Example 1 | 98.0 | 88.7 | 1.93 | 0.15 |
| Example 4 | 98.1 | 82.8 | 2.17 | 0.1 or less |

Referring to Table 4, the conversion ratio of L-ethyl lactate was 98.0% and the selectivity to each of L-lactide, Meso-lactide and D-lactide was 88.7%, 1.93% and 0.15%, respectively, in case of Example 1 in which titanium ethoxide was used. Meanwhile, in case of Example 4 in which titanium tetrachloride was used, the conversion ratio of L-ethyl lactate was 98.1% and the selectivity to each of L-lactide, Meso-lactide and D-lactide was 82.8%, 2.17% and 0.1% or less, respectively.

Upon comparing Example 1 using titanium ethoxide with Example 4 using titanium tetrachloride, it can be found that Example 1 shows a little higher selectivity to L-lactide.

Test Example 5

Analyses of Conversion Ratio and Selectivity According to Catalysts

To analyze conversion ratio and selectivity when the titanium-based catalyst and the tin-based catalyst as a comparative catalyst are respectively used, the reaction products were analyzed using gas chromatography, and the results are shown in Table 5.

TABLE 5

| Examples | Conversion ratio L-ethyl lactate | Selectivity (%) | | |
|---|---|---|---|---|
| | | L-lactide | Meso-lactide | D-lactide |
| Example 1 | 98.0 | 88.7 | 1.93 | 0.15 |
| Comparative Example 2 | 86.7 | 50.3 | 1.23 | 0.10 |

Referring to Table 5, the conversion ratio of L-ethyl lactate was 98.0% and the selectivity to each of L-lactide, Meso-lactide and D-lactide was 88.7%, 1.93% and 0.15%, respectively, in case of Example 1 in which the catalyst according to the present disclosure was used. Meanwhile, in case of Comparative Example 2 in which the tin octanoate compound was used, the conversion ratio of L-ethyl lactate was 86.7% and the selectivity to each of L-lactide, Meso-lactide and D-lactide was 50.3%, 1.23% and 0.10, respectively.

Accordingly, it can be found that when lactides are produced using a titanium-based catalyst according to the present disclosure, conversion ratio of L-ethyl lactate as well as selectivity to L-lactide increases so that lactides can be efficiently produced, as compared with the case of using a tin-based catalyst which is used as a catalyst for polymerizing lactic acid and an ester of lactic acid.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method for directly producing a lactide, the method comprising:

performing a transesterification reaction between two molecules of an ester of lactic acid having the following Chemical Formula (1) included in a starting material under an inert environment, in the presence of a titanium-based catalyst which includes at least one member selected from the group consisting of titanium tetraalkoxides having the formula $(R'O)_4Ti$ in which R' is a lower alkyl group having 1 to 4 carbon atoms, titanium halides having the formula $TiX_4$ or $TiX_3$ in which X=F, Cl or Br, alkoxy titanium halides having the formula $(R'O)_{4-x}TiX_x$ in which X=F, Cl, or Br, x =1 to 3 and R' is as defined above, titanium acetylacetonates having the formula $Ti(acetylacetonate)_2$, and titanium alkoxide acetylacetonates having the formula $Ti(acetylacetonate)(OR')_2$ in which R' is as defined above, or a catalyst mixture containing the titanium-based catalyst, to produce a lactide of the following Chemical Formula (2) while simultaneously removing an alcohol of the formula ROH generated as a by-product, according to the following Reaction Scheme 1:

<Reaction Scheme 1>

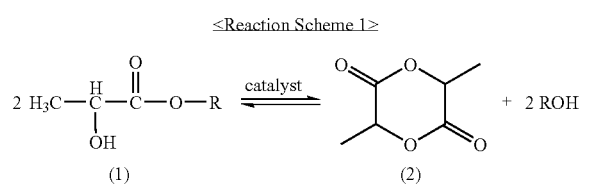

wherein R is a lower alkyl group having 1 to 4 carbon atoms.

2. The method according to claim 1, wherein the starting material further comprises 20% by weight or less of a lactic acid, an oligomer of lactic acid, or a mixture thereof.

3. The method according to claim 1, wherein the titanium-based catalyst further includes a compound of the following Chemical Formula (5) or Chemical Formula (6):

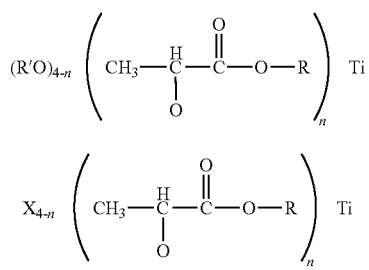

wherein
each of R and R' is independently a lower alkyl group having 1 to 4 carbon atoms;
X is a halogen; and
n is an integer of 1 to 4.

4. The method according to claim 1, wherein the catalyst mixture containing the titanium-based catalyst further comprises 0.1 to 30% by weight of at least one member selected from the group consisting of aluminum (Al), silicon (Si), tin (Sn), zirconium (Zr), niobium (Nb), molybdenum (Mo), tungsten (W), yttrium (Y), gallium (Ga) and a mixture thereof which are capable of forming an alkoxide, in addition to the titanium-based catalyst.

5. The method according to claim 1, wherein an amount of the titanium-based catalyst or the catalyst mixture containing the titanium-based catalyst used in the reaction is 0.01 to 10 mole% with respect to the ester of lactic acid.

6. The method according to claim 5, wherein the amount of the titanium-based catalyst or the catalyst mixture containing the titanium-based catalyst used in the reaction is 0.05 to 3 mole% with respect to the ester of lactic acid.

7. The method according to claim 1, wherein the ester of lactic acid as the starting material is used in a single isomeric form of either L-form or D-form optical isomer thereof.

8. The method according to claim 1, wherein a temperature of the transesterification reaction is gradually increased starting from a temperature lower than a boiling point of the ester of lactic acid as the starting material.

9. The method according to claim 8, wherein the reaction temperature ranges from 30 to 250° C.

10. The method according to claim 9, wherein the reaction temperature ranges from 70 to 180° C.

11. The method according to claim 1, wherein the reaction is performed at a reduced pressure condition in the range of 1 to 750 mmHg.

12. The method according to claim 11, wherein the reduced pressure condition in the reaction ranges from 20 to 700 mmHg.

13. The method according to claim 1, wherein the ester of lactic acid as the starting material is intermittently fed into the reaction system as the reaction time passes.

14. The method according to claim 13, wherein a feeding rate of the ester of lactic acid as the starting material is 10 to 300 molar ratio of the ester of lactic acid per one mole of the catalyst per hour, based on the ester of lactic acid.

15. The method according to claim 14, wherein the feeding rate of the ester of lactic acid as the starting material is 30 to 200 molar ratio of the ester of lactic acid per one mole of the catalyst per hour, based on the ester of lactic acid.

16. The method according to claim 1, wherein a solvent having a boiling point higher than that of the ester of lactic acid is used in order to proceed the reaction smoothly by avoiding that a condensation reaction is inhibited by the lactide produced by the transesterification reaction.

17. The method according to claim 16, wherein the solvent is selected from the group consisting of tri ethyleneglycol dimethyl ether, tetraethyleneglycol dimethyl ether, γ-butyrolactone and dimethyl ether.

18. The method according to claim 1, the lactide produced by the reaction retains an optical property of the ester of lactic acid as the starting material.

* * * * *